(12) United States Patent
Wang

(10) Patent No.: US 10,625,053 B2
(45) Date of Patent: Apr. 21, 2020

(54) TRACHEOSCOPE PULL WIRE CONTROL MECHANISM

(71) Applicant: Zhuhai Kaden Medical Imaging Technology Co., Ltd, Zhuhai, Guangdong (CN)

(72) Inventor: Nanbing Wang, Guangdong (CN)

(73) Assignee: Zhuhai Kaden Medical Imaging Technology Co., Ltd, Zhuhai (CN)

( * ) Notice: Subject to any disclaimer, the term of this patent is extended or adjusted under 35 U.S.C. 154(b) by 0 days.

(21) Appl. No.: 15/879,465

(22) Filed: Jan. 25, 2018

(65) Prior Publication Data

US 2018/0207401 A1 Jul. 26, 2018

(30) Foreign Application Priority Data

Jan. 25, 2017 (TW) .............................. 106102870 A
Jan. 25, 2017 (TW) .............................. 106201407 U

(51) Int. Cl.

| A61M 25/01 | (2006.01) |
|---|---|
| A61B 1/267 | (2006.01) |
| A61B 1/005 | (2006.01) |
| A61M 16/04 | (2006.01) |
| A61B 1/00 | (2006.01) |

(52) U.S. Cl.
CPC ....... *A61M 25/0136* (2013.01); *A61B 1/0052* (2013.01); *A61B 1/267* (2013.01); *A61M 16/0472* (2013.01); *A61B 1/00006* (2013.01); *A61B 1/0057* (2013.01); *A61M 25/0147* (2013.01)

(58) Field of Classification Search
CPC .......... A61M 25/0133; A61M 25/0136; A61M 25/0147; A61M 16/0472; A61B 1/267; A61B 1/0052; A61B 1/0057
See application file for complete search history.

(56) References Cited

U.S. PATENT DOCUMENTS

| 5,462,527 A | * | 10/1995 | Stevens-Wright ......................... A61B 18/1492 600/585 |
|---|---|---|---|
| 5,626,553 A | * | 5/1997 | Frassica ............... A61B 1/0052 600/146 |
| 5,888,192 A | * | 3/1999 | Heimberger ......... A61B 1/0052 600/146 |
| 8,790,250 B2 | * | 7/2014 | Petersen .............. A61B 1/0052 600/146 |

(Continued)

FOREIGN PATENT DOCUMENTS

CN 102271572 A 12/2011

*Primary Examiner* — Nicholas J Plionis
*Assistant Examiner* — Steven J Cotroneo

(57) ABSTRACT

A tracheoscope pull wire control mechanism includes a rotating wheel pivotally arranged inside a handle; a holding cavity is formed on an upper portion of the rotating wheel; a spring and a brake block are arranged in the groove, such that a connection rod of the control piece above the handle passes through a long slotted hole at a position opposite to the handle, and is clamped and linked with the brake block; and the near ends of the two pull wires are extended and are combined on the rotating wheel of the control mechanism. The positioning structure can be operated with a single hand, which is different from the conventional two-hand control manner; and the operation efficiency and the convenience are improved.

3 Claims, 3 Drawing Sheets

(56) References Cited

U.S. PATENT DOCUMENTS

| | | | | |
|---|---|---|---|---|
| 9,022,976 | B2* | 5/2015 | Tegg | A61B 1/00133 604/95.04 |
| 9,125,582 | B2* | 9/2015 | Petersen | A61B 1/0008 |
| 9,657,817 | B2* | 5/2017 | Asselin | F16H 21/40 |
| 9,968,241 | B2* | 5/2018 | Iuel | A61B 1/0052 |
| 10,136,800 | B2* | 11/2018 | Hatano | G02B 23/24 |
| 10,219,682 | B2* | 3/2019 | Hatano | A61B 1/0052 |
| 2007/0255104 | A1* | 11/2007 | Maruyama | A61B 1/0052 600/148 |
| 2016/0341241 | A1* | 11/2016 | Hosaka | A61B 1/0052 |
| 2016/0360952 | A1* | 12/2016 | Yamanaka | A61B 17/29 |
| 2018/0049625 | A1* | 2/2018 | Nakade | A61B 1/00071 |
| 2018/0183179 | A1* | 6/2018 | Byrd | H01R 39/02 |
| 2019/0014974 | A1* | 1/2019 | Hatano | A61B 1/00 |
| 2019/0076093 | A1* | 3/2019 | Saroha | A61M 25/0113 |

* cited by examiner

TRACHEOSCOPE PULL WIRE CONTROL MECHANISM

CROSS REFERENCE TO RELATED APPLICATIONS

The present application claims the benefit of Taiwanese Patent Application Nos. 106201407 and 106102870 filed on Jan. 25, 2017. All the above are hereby incorporated by reference.

TECHNICAL FIELD

The invention is a tracheoscope pull wire control mechanism, and mainly provides a simple and convenient control mechanism which can achieve the effect of linking the far end of a catheter of a tracheoscope to swing and bend by means of operating and moving a control piece above a handle to drive displacements of pull wires; particularly, with a structural design for positioning, the swing control range of the far end can be fixed, such that the operation convenience is increased and the progressive practicability is achieved.

BACKGROUND

A tracheoscope structure generally includes an elongated catheter so as to extend into a human body. The far end of the catheter is combined with a shooting module, so as to shoot an image in a human body cavity and send the image to an external screen, and therefore a medical staff observes or gives treatment directly. In order to get images at different angular positions inside the human body, a hose structure that may be bent is arranged at the far end of the catheter, so as to control the swing using two pull wires and link the shooting module to rotate, thereby obtaining multiple intracavitary images at different angles.

An early mechanism for linking the pull wires is arranged on an upper portion of a handle at the near end of the tracheoscope. A knob mechanism that can be operated by a user on the handle is provided so as to link pull wires to control the swing of the far end of the catheter. However, there is a need to use both hands to control cooperatively, that is, one hand holds the handle, and the other hand implements a locking or tightening action, such that the bending angle of the far end of the catheter can be positioned, which is very inconvenient.

Then, there is an improved design of the control mechanism using a single hand operation. For example, for Chinese application No. 200980153972.1, entitled "Mechanism for Controlling Bending Section of Endoscope", a movable button is arranged outside a handle and is utilized to link a cross rod piece inside to drive movements of the pull wires, such that the far end of a pipe of the tracheoscope may be controlled to swing. However, the operation of the control mechanism still is not convenient enough. When an operator pushes the button such that the far end of the catheter is bent to be positioned, it is essential to press a clamping mechanism again to lock the button. When there is a need to change an angle of the far end of the catheter, the unlocking action is operated additionally, which brings very inconvenient troubles for a physician who must highly focus on observing the image and performing the operation, and is difficult to achieve the purpose of the single hand operation in well-known patents. Hence, it is necessary to make improvements.

SUMMARY

The invention is a tracheoscope pull wire control mechanism, and mainly provides a simple and convenient control mechanism. By moving a control piece above a handle to drive pull wires to generate a displacement, the far end of a catheter of a tracheoscope is linked to swing and bend. A structure mainly includes a rotating wheel pivotally arranged inside a handle; a holding cavity is formed on an upper portion of the rotating wheel; a spring and a brake block are arranged in the groove; a connection rod of the control piece above the handle passes through a long slotted hole at a position opposite to the handle, and is clamped and linked with the brake block; and the near ends of the two pull wires are extended and are combined on the rotating wheel of the control mechanism. Therefore, after the control piece is pressed simply, the pull wires are linked via a simple operation in a manner of moving back and forth, thereby achieving the purpose of enabling the far end of the catheter to bend to different directions. As long as a pressing finger is released, the far end of the catheter can be positioned at the angular position, achieving an obvious progress.

Reference numbers are set forth hereinafter:
1 a handle; 11 a spherical body; 12 a long slot; 2 a rotating wheel; 21 a holding groove; 3 a brake block; 31 a spring; 32 a non-slip piece; 33 a central hole; 4 a control piece; 41 a connection rod; 5 a pull wire

DETAILED DESCRIPTION OF THE EMBODIMENTS

Figure 1:
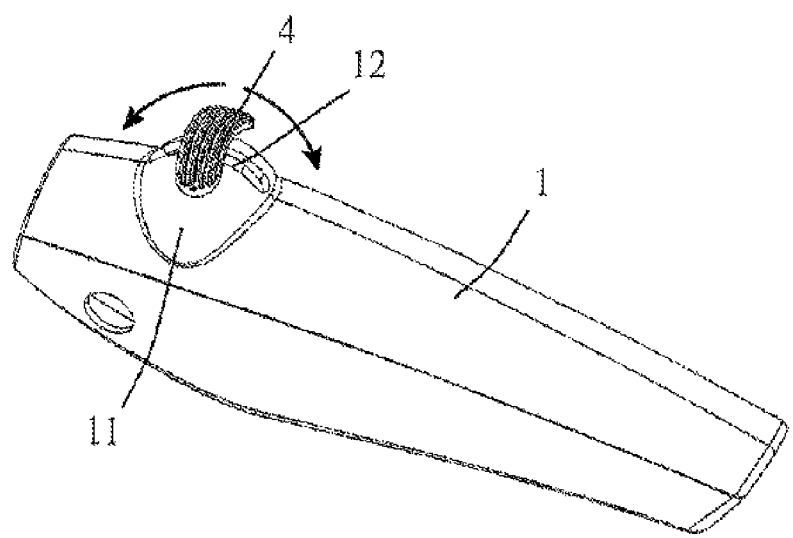
FIG. 1 is an external stereoscopic diagram of a tracheoscope handle of the invention.
Figure 2:
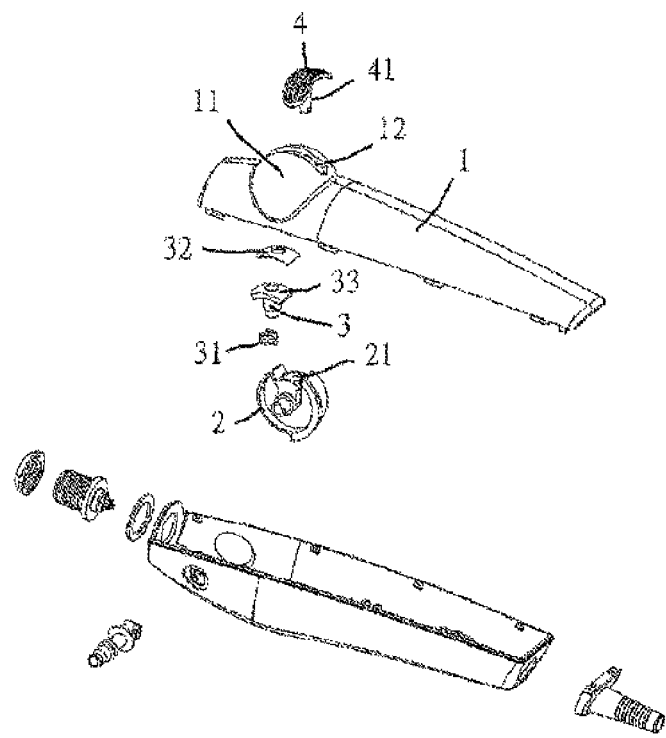
FIG. 2 is a breakdown stereoscopic diagram of a tracheoscope handle and a control mechanism of the invention.
Figure 3:
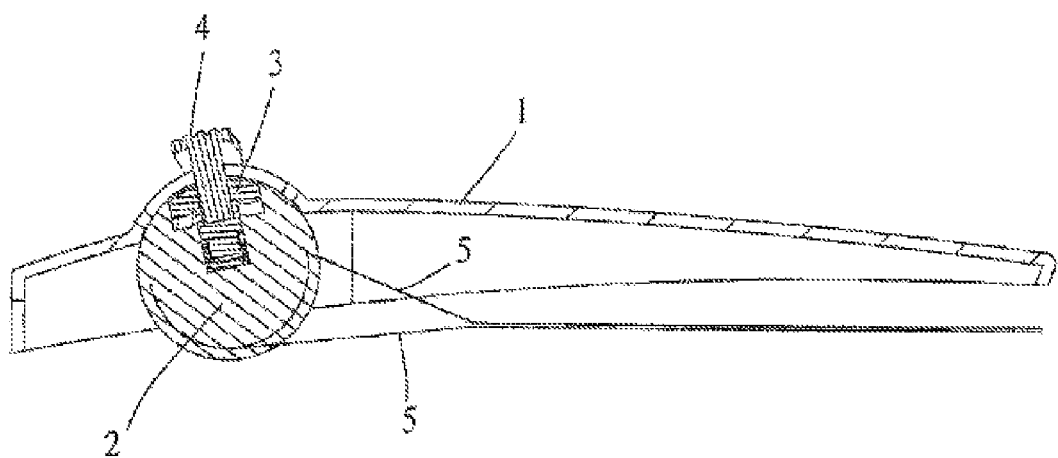
FIG. 3 is a cross-section diagram of FIG. 1 of the invention.

Please referring to FIG. 1-3, the embodiment is an tracheoscope pull wire control mechanism, which is mainly arranged inside a handle 1; a structure includes a rotating wheel 2, which is pivotally arranged in an internal space of the handle 1 to form a rotatable structure; a holding groove 21 is formed on an upper portion of the rotating wheel 2; a spring 31 and a brake block 3 are arranged in the groove; an upper portion of the brake block 3 is of an arc shape and is combined with a non-slip piece 32; an upper portion of the handle 1, relative to the rotating wheel 2, which is arranged into a spherical body 11, and is provided with a longitudinal long slotted hole 12; a control piece 4 is arranged above the spherical body 11 of the handle 1 and is provided with a connection rod 41 thereunder, such that the connection rod 41 passes through the long slotted hole 12 and is combined and fixed with a central hole 33 of the brake piece 3 thereunder; and thus, through the movement of the control piece 4, the rotation of the brake block 3 to the rotating wheel 2 is controlled. Additionally, the near ends of two pull wires 5 of the tracheoscope are extended and are combined on the rotating wheel 2 of a control mechanism.

Figure 4:
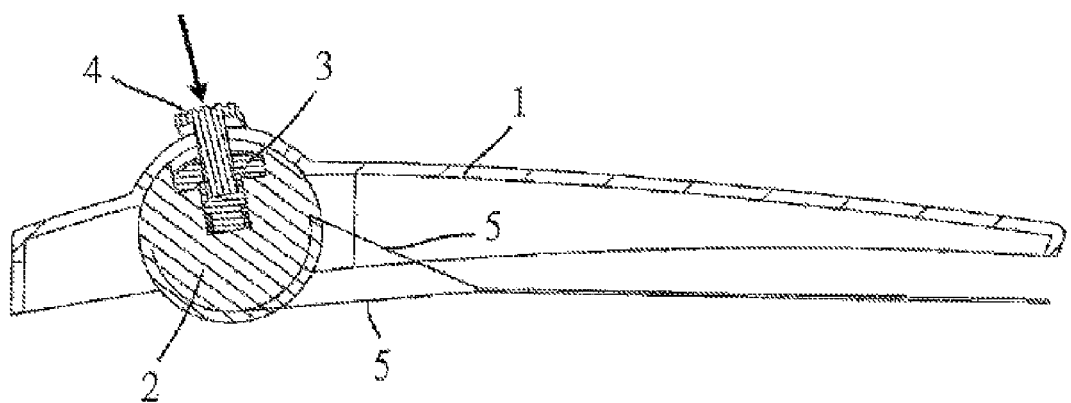
FIG. 4 is a state diagram after pressing of FIG. 3 of the invention.
Figure 5:
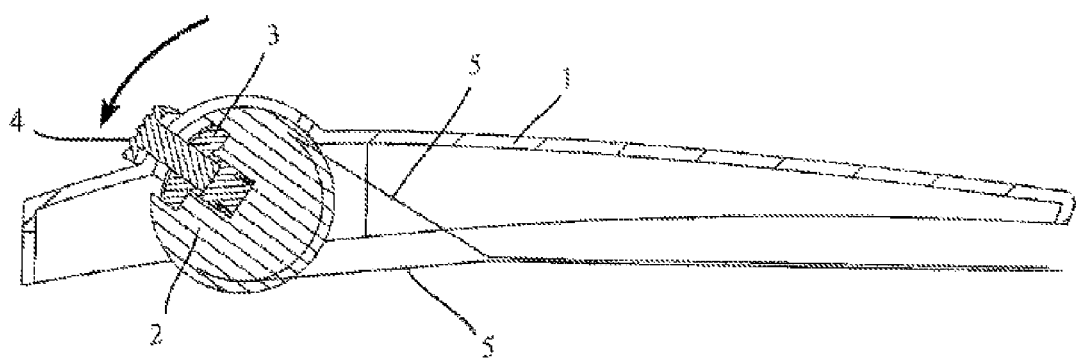
FIG. 5 and FIG. 6 are state diagrams of an embodiment of the invention in which a control piece is moved back and forth as shown in FIG. 4.
Figure 6:
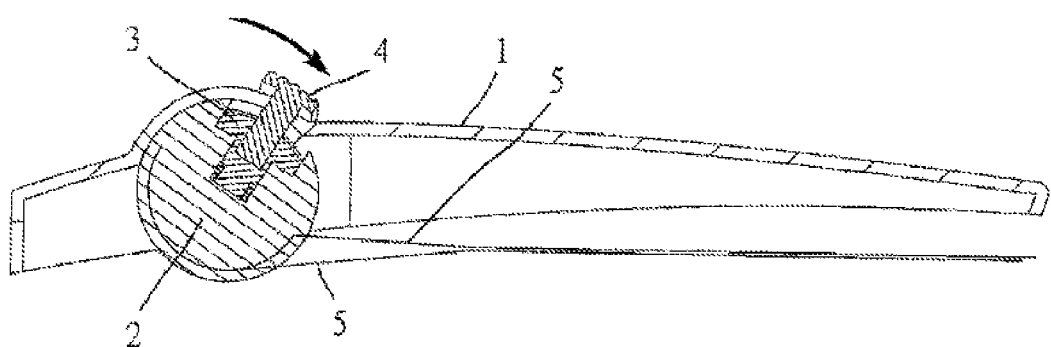

When the tracheoscope pull wire control mechanism is used, an operator can simply press the control piece 4, such that the brake block 4 downwardly compresses the spring 31, and the non-slip piece 32 leaves away from the inner surface of the spherical body 11. As shown in FIG. 4, the control piece 4 can be operated easily to move back and forth so as to drive the rotating wheel 1 to rotate forwardly and reversely, thereby achieving the purpose of controlling relative positions of the linked two pull wires 5 and thus enabling the far end of the catheter to bend toward different directions. As shown in FIG. 5 and FIG. 6, with such an operating manner, the operator can implement easily only with a single hand without distraction. When the far end of the catheter is bent to a certain special angle, as long as the pressing finger is released, the spring 31 pushes the brake block 3 upward by a restoring force and the non-slip piece 32 is tightly attached to the inner surface of the spherical body 11. Returning to a position as shown in FIG. 3, the positioning effect like a brake is obtained. When the rotating wheel 3 is fixed at this position, the effect of positioning the far end of the catheter at the bending angle is achieved. The operator does not need to spend a mind and a power for maintenance, and can observe an image obtained at this angle wholeheartedly and stably and can give the medical treatment, achieving the progressive and practical values of the invention.

In conclusion, the improved control mechanism of the invention can support the operator to simply and conveniently control the far end of the catheter of the tracheoscope to bend and swing with a single hand and may fix them at the selected angle and position. The invention has excellent progress and practicability compared with the current design.

What is claimed is:

1. A tracheoscope pull wire control mechanism, which is arranged inside a handle of a tracheoscope and is characterized by comprising:

a rotating wheel, which is pivotally arranged in an internal space of the handle to form a rotatable structure, a holding groove being formed on an upper portion of the rotating wheel;

a brake block, which is arranged in the holding groove of the rotating wheel and is provided with a spring thereunder and a central hole, an upper portion of the brake block being of an arc shape and being additionally combined with a non-slip piece;

an upper portion of the tracheoscope handle, relative to the rotating wheel, being arranged into a spherical body structure, and being provided with a longitudinal long slotted hole;

a control piece, which is arranged above the spherical body of the handle, and is provided with a connection rod thereunder, the connection rod passing through the long slotted hole on the spherical body, and being combined with the central hole of the brake piece thereunder; and near ends of two pull wires of the tracheoscope, being extended and being combined on the rotating wheel of the control mechanism;

wherein when the control piece is not pressed, the non-slip piece on the brake block is tightly attached to an inner surface of the spherical body of the handle via an upward elastic force of the spring, such that the rotating wheel, the pull wires, and a far end of a catheter all are in a stable positioned state; and when the control piece is pressed, the non-slip piece leaves away from the inner surface of the spherical body.

2. The tracheoscope pull wire control mechanism as claimed in claim 1, wherein when the control piece is pressed such that the tracheoscope pull wire control mechanism is moved back and forth, the brake block can be linked to drive the rotation of the rotating wheel and to change relative positions of the pull wires, thereby enabling the far end of the catheter of the tracheoscope to generate a bending angle.

3. The tracheoscope pull wire control mechanism as claimed in claim 1, wherein the spring is a coil spring, and the coil spring and the connection rod are coaxially arranged.

* * * * *